(12) United States Patent
Randall et al.

(10) Patent No.: US 12,390,246 B2
(45) Date of Patent: Aug. 19, 2025

(54) DUAL ACCESS INCISING CATHETER

(71) Applicant: C.R. Bard, Inc., Tempe, AZ (US)

(72) Inventors: Michael Randall, Gilbert, AZ (US);
Chad Van Liere, Phoenix, AZ (US);
Andrzej J. Chanduszko, Chandler, AZ (US)

(73) Assignee: C.R. Bard, Inc., Tempe, AZ (US)

( * ) Notice: Subject to any disclaimer, the term of this patent is extended or adjusted under 35 U.S.C. 154(b) by 249 days.

(21) Appl. No.: 17/086,570

(22) Filed: Nov. 2, 2020

(65) Prior Publication Data

US 2021/0045769 A1 Feb. 18, 2021

Related U.S. Application Data

(63) Continuation of application No. 15/859,461, filed on Dec. 30, 2017, now Pat. No. 10,820,921.

(51) Int. Cl.
| | | |
|---|---|---|
| *A61B 17/3207* | (2006.01) | |
| *A61B 17/22* | (2006.01) | |
| *A61M 25/10* | (2013.01) | |
| *A61B 17/00* | (2006.01) | |
| *A61M 25/00* | (2006.01) | |

(52) U.S. Cl.
CPC ...... *A61B 17/320725* (2013.01); *A61B 17/22* (2013.01); *A61M 25/104* (2013.01); *A61B 2017/00778* (2013.01); *A61B 2017/22038* (2013.01); *A61B 2017/22051* (2013.01); *A61B 2017/22061* (2013.01); *A61B 2017/320741* (2013.01); *A61B 2217/007* (2013.01); *A61M 2025/0095* (2013.01); *A61M 2025/0096* (2013.01); *A61M 2025/109* (2013.01)

(58) Field of Classification Search
CPC ............ A61B 17/320725; A61B 17/22; A61B 2017/00778; A61B 2017/22038; A61B 2017/22051; A61B 2017/22061; A61B 2017/320741; A61B 17/3207; A61B 2017/320766; A61M 25/104
See application file for complete search history.

(56) References Cited

U.S. PATENT DOCUMENTS

| | | | | |
|---|---|---|---|---|
| 5,873,852 | A * | 2/1999 | Vigil ................... | A61M 25/10 604/509 |
| 2003/0120208 | A1* | 6/2003 | Houser ................. | A61F 2/95 604/103.04 |
| 2004/0034384 | A1* | 2/2004 | Fukaya ............... | A61M 25/104 606/191 |
| 2007/0106215 | A1* | 5/2007 | Olsen .................. | A61M 25/104 606/167 |
| 2009/0171284 | A1* | 7/2009 | Burke ................. | A61M 25/104 604/104 |

(Continued)

FOREIGN PATENT DOCUMENTS

JP 2009527316 A 7/2009

*Primary Examiner* — Kathleen S Holwerda
(74) *Attorney, Agent, or Firm* — Andrew D. Dorisio; Dickinson Wright PLLC

(57) ABSTRACT

Dual-access site catheter systems with a blade or scoring functionality entering through a first access site and a balloon functionality for manipulating or driving the blade or scoring functionality through a different site. The blade or scoring functionality also sometimes provides needle or fluid delivery functionality to an atherosclerotic lesion.

11 Claims, 7 Drawing Sheets

(56) References Cited

U.S. PATENT DOCUMENTS

| | | | | |
|---|---|---|---|---|
| 2012/0130409 A1* | 5/2012 | Schur | ............... | A61M 25/104 |
| | | | | 606/159 |
| 2013/0041391 A1* | 2/2013 | Spencer | ......... | A61B 17/320725 |
| | | | | 606/159 |
| 2016/0249942 A1* | 9/2016 | Olson | ............... | A61M 25/104 |
| | | | | 604/509 |
| 2017/0100570 A1* | 4/2017 | Giasolli | ............ | A61M 25/1002 |

* cited by examiner

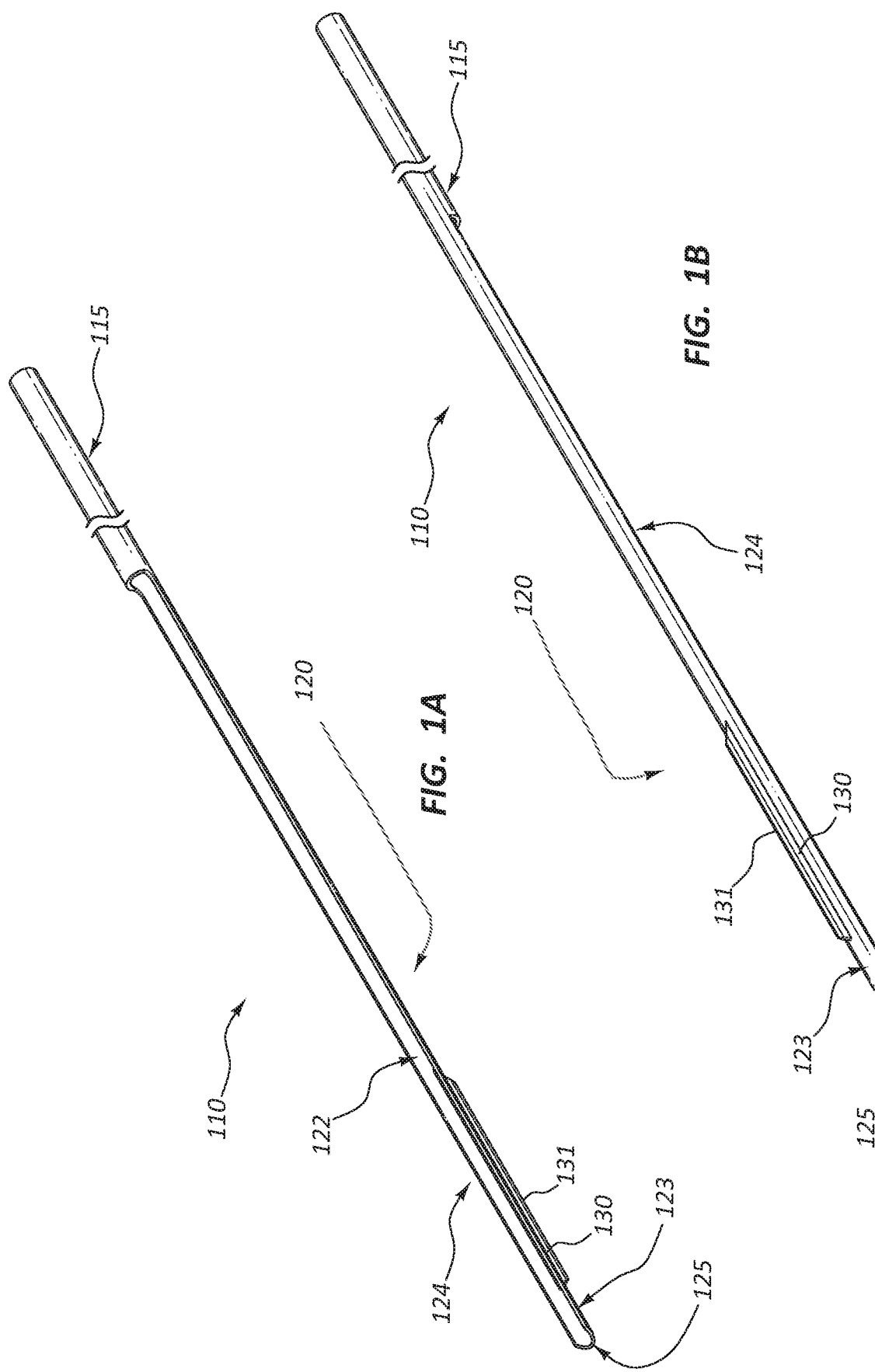

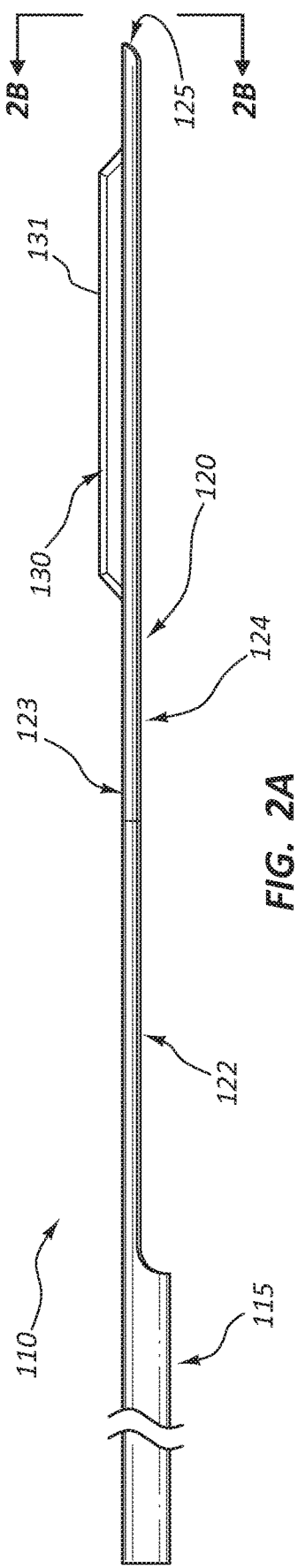
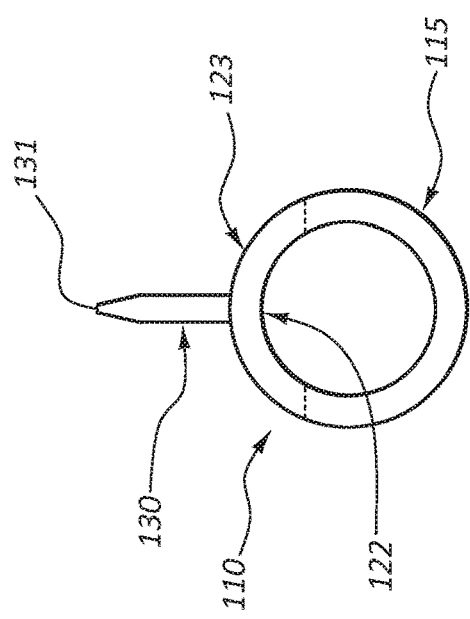
FIG. 2A
FIG. 2B

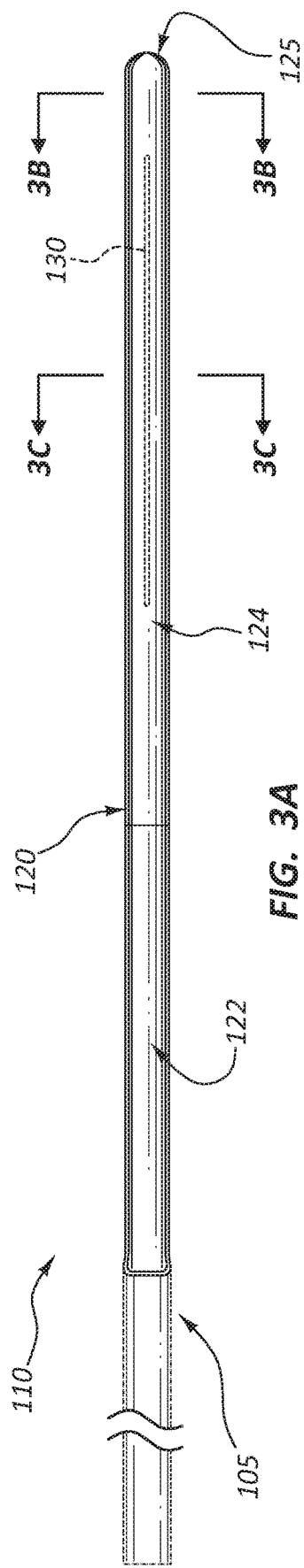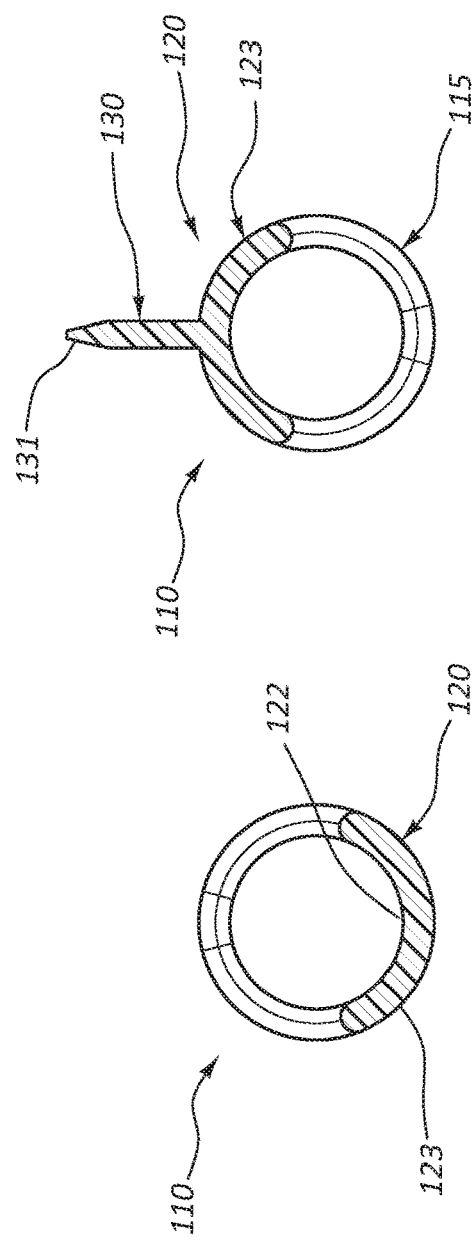
FIG. 3A
FIG. 3B
FIG. 3C

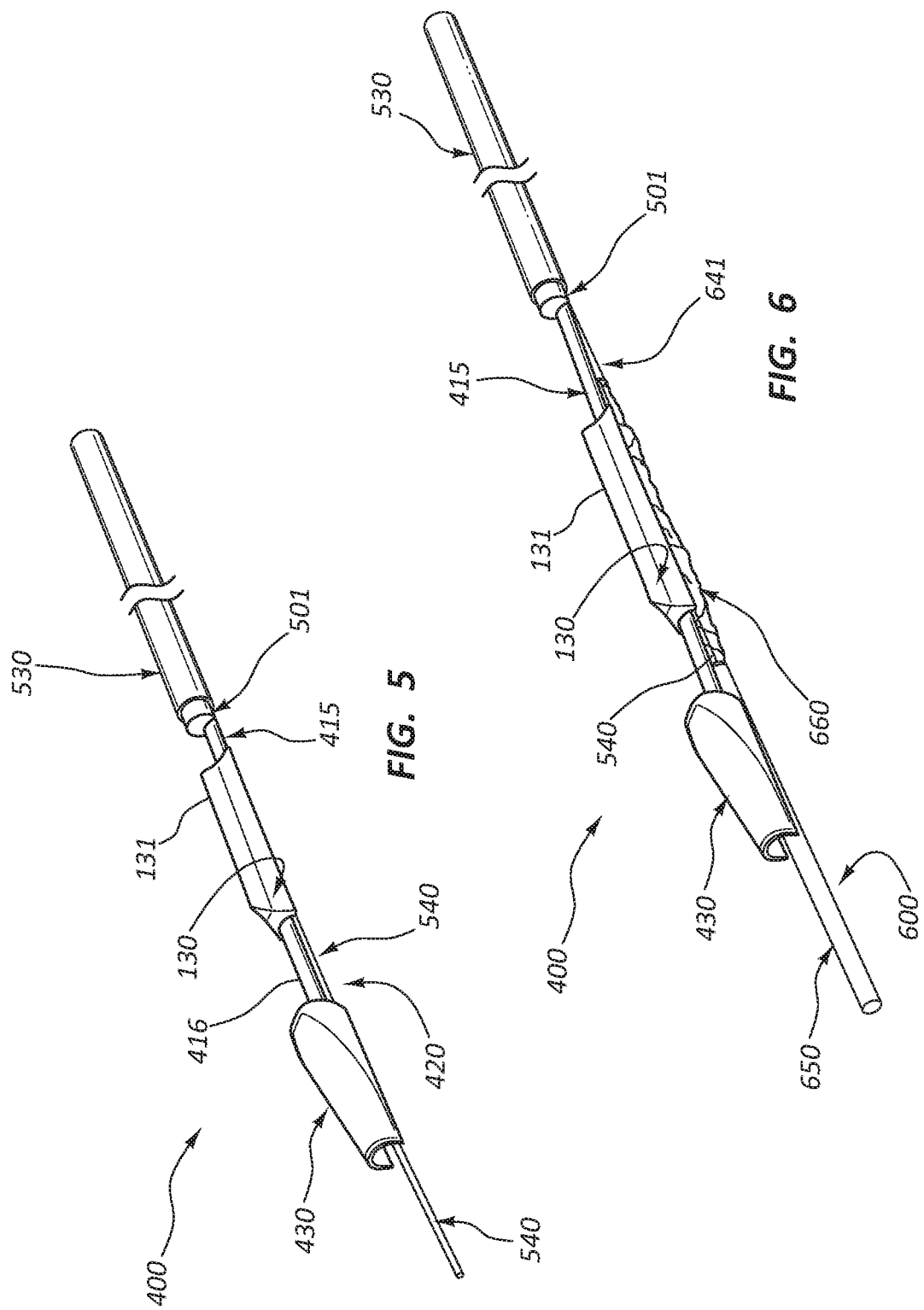

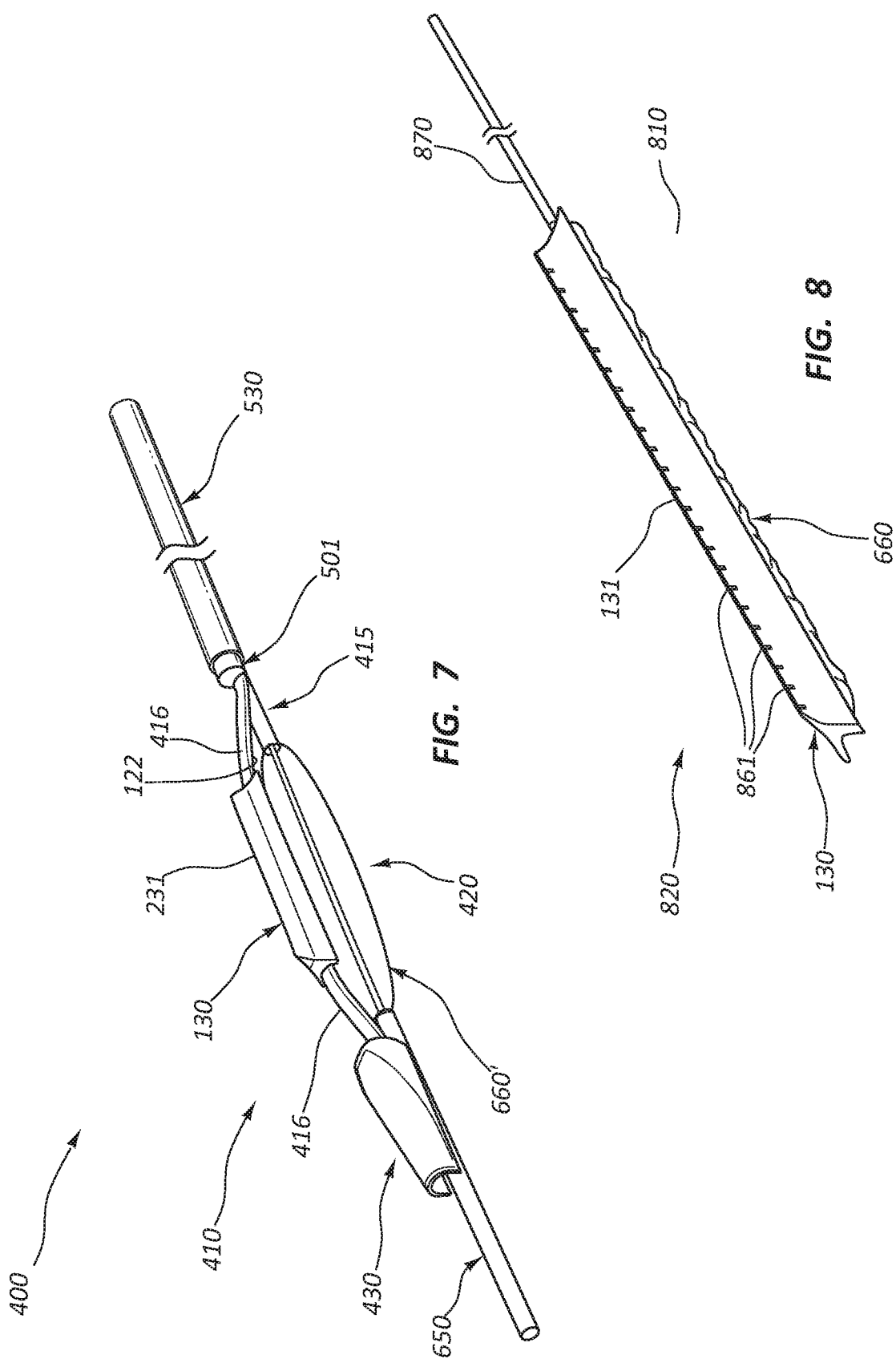

DUAL ACCESS INCISING CATHETER

BACKGROUND

Various medical conditions can affect human vasculature. Commonly, atherosclerosis narrows arteries at a location called a lesion or stenosis. Arteriosclerotic lesions form on vessel walls and block or restrict blood flow.

Different types of arteriosclerotic lesions come in different forms. Some forms may impede blood flow and may have a calcified or fibrous nature. Eventually, the lesion weakens surrounding arterial tissue, and sometimes this tissue ruptures.

Balloon angioplasty and stenting procedures treat arteriosclerotic lesions. Along with other angioplasty procedures, balloon catheters are used in below-the-knee (BTK) and narrow-vessel angioplasty. These types of angioplasty are used to treat diseases, such as peripheral artery disease (PAD). The incidence of PAD continues to increase leading to increased demand for useful treatments.

Angioplasty procedures have become a popular alternative for treating lesions caused by PAD because angioplasty procedures are considerably less invasive than other alternatives. For example, PAD-causing lesions can be treated with bypass surgery. But bypass surgery is very risky and invasive and requires long recovery times. Typically, bypass surgery involves opening the peripheral vasculature and grafting a replacement vessel around the blockage or lesion.

In balloon angioplasty, a catheter with a balloon is placed into the patient's vessel. The balloon presents a low profile that can fit through smaller vessels. Once positioned across a lesion, the balloon is inflated using inflation fluid. As the balloon inflates, it presses against the vessel wall and radially expands or effaces the lumen to partially or completely open the vessel.

Many target lesions contain calcified or fibrous plaque or necrotic tissue. These stenoses may be difficult to fully expand using conventional balloons because conventional balloons sometimes do not supply enough outward pressure upon inflation. Also, target arteries frequently respond to an angioplasty procedure with vessel recoil.

Currently, slicing and cutting technologies are used in angioplasty. This technology uses some sort of aid or force focusing device to cut or crack a target lesions but currently useful devices are too large for below-the-knee or small vessel angioplasty and devices for this narrower (4-5 French) range are limited. Slicing or cutting BTK lesions needs pressures comparable to larger vessels, but the space that the operator has to work in is much smaller. Typically, treatment devices employ fixed blades or wires either bonded to or disposed directly on balloons or bonded to deployment arms that are pulled through the lesions to cut them. Treatment of BTK and small-vessel lesions needs lower profile systems as physicians seek to access narrower and narrower vessels, such as below-the-knee vessels, in the vessels of small or pediatric patients.

SUMMARY

Some variations of the disclosed dual-access angioplasty system comprise two complementary catheters a type-1 catheter that has typical catheter-like components. The type-1 catheter has a proximal end that remains outside of a patient's body, and a distal end configured to deliver a force focusing means such as a protrusion, blade(s), teeth, or needles to the inner surface of an atherosclerotic lesion. The type-1 catheter has a guidewire lumen arranged as in a typical over-the-wire delivery system. In other variations, the guidewire lumen is arranged as in a typical rapid exchange delivery system. A tailpiece serves as the distal end of the type-1 catheter. A tailpiece proximal end connects to the type-1 proximal end and a tailpiece distal end has a push region opposite of a protrusion in which the push region comprises a balloon pocket. Portions of the tailpiece distal end are responsive to an outwardly acting force to move from a relaxed configuration to an activated configuration.

In these or other variations, the push region has a shape that is complementary to an angioplasty balloon. In some variations, when portions of the tailpiece are in a relaxed configuration, the protrusion supplies substantially no force to a vessel wall. In these or other variations, when portions of the tailpiece are in the activated configuration, the protrusion supplies operative force to the vessel wall. In some variations, the protrusion comprises a blade with an edge. In these or other variations, the type-1 catheter does not include an angioplasty balloon. In some variations comprising a blade with an edge, the edge has openings. In these or other variations, the type-1 catheter has an injection tube in fluid communication with the openings and the type-1 proximal end. Sometimes, the blade connects to the tailpiece distal end through a flexible support.

In these or other variations, an angioplasty balloon supplies the outwardly acting force and the type-1 catheter does not have an angioplasty balloon.

In these or other variations, the protrusion has needle projections. In some of these variations, the needle projections are in fluid communication with the type-1 proximal end. Sometimes, the protrusion connects to the tailpiece distal end through a flexible support.

Moreover, in some variations, a system is disclosed. The system has a guidewire, a type-1 catheter with a guidewire lumen, a type-1 proximal end, and a tailpiece. The tailpiece comprises a tailpiece proximal end connecting the tailpiece to a distal end of the type-1 catheter proximal end, a tailpiece distal end, a protrusion extending radially outward from the tailpiece distal end with a push region opposite the protrusion. The push region has a balloon pocket and the tailpiece distal end has a relaxed configuration responsive to outwardly or radially outwardly acting force to move to an activated configuration. The system also has a type-2 catheter having a body, an angioplasty balloon disposed on the distal end of the body, and a guidewire lumen associated with the body and the push region and the angioplasty balloon have shapes complementary to each other.

In these or other variations, the protrusion is a blade with an edge. And in the relaxed configuration, the protrusion supplies substantially no force to a vessel wall, and in the activated configuration, the protrusion supplies operative force to the vessel wall.

In these or other variations, the edge has openings in fluid communication with the proximal end of the type-1 catheter.

Alternatively, in some variations the protrusion comprises needle projections. In the relaxed configuration, the needle projections supply substantially no force to a vessel wall, and in the activated configuration the needle projections supply operative force to the vessel wall. In these or other systems, the angioplasty balloon supplies the outwardly acting force.

BRIEF DESCRIPTION OF FIGURES

FIG. 1A is a perspective view of the bottom of a tailpiece of a type-1 catheter.

FIG. 1B is a top view of the tailpiece of FIG. 1A.

FIG. 2A is a side view of the tailpiece of FIG. 1A.

FIG. 2B is a cross-section of an end view of the tailpiece of FIG. 1A along section line 2B.

FIG. 3A is a top view of the tailpiece of FIG. 1A.

FIG. 3B is a cross-section view as indicated at section line 3B.

FIG. 3C is a cross-section view as indicated at section line 3C.

FIG. 5 is another perspective view of an alternative version of a type-1 catheter.

FIG. 6 is yet another perspective view of an alternative version of a type-1 catheter.

FIG. 7 is a perspective view of a type-1 and a type-2 catheter.

FIG. 8 is a perspective view of a fluid delivery version of a type-1 catheter blade.

Figure 4:
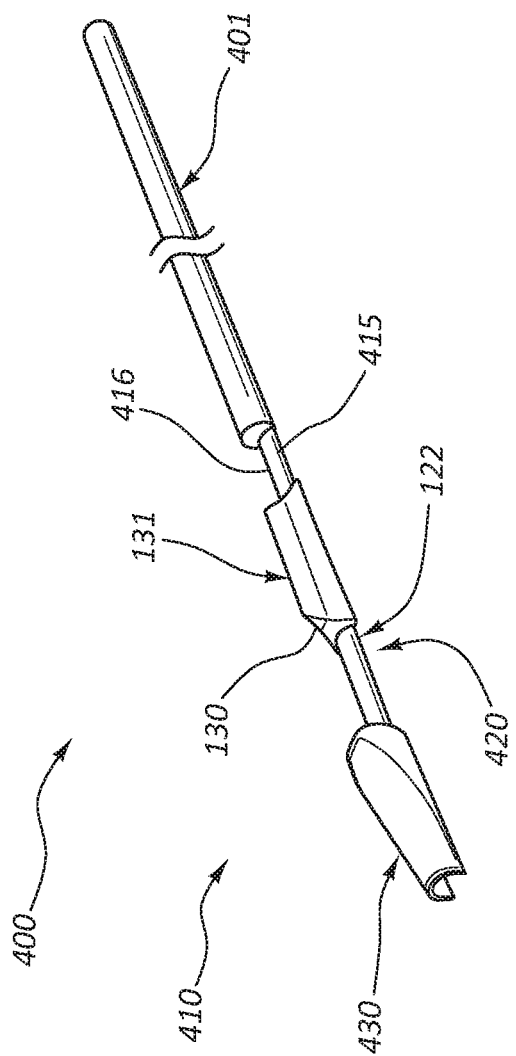
FIG. 4 is a perspective view of an alternative version of a type-1 catheter.

DETAILED DESCRIPTION 110 tailpiece
115 tailpiece proximal end
120 tailpiece distal end
122 push region
123 tailpiece distal end outer surface
124 balloon pocket
125 distal catheter tip
130 protrusion or blade
131 edge
400 type-1 catheter
401 catheter body
410 tailpiece
415 tailpiece proximal end
416 flexible support
420 tailpiece distal end
425 distal catheter tip
430 nose
501 catheter body
530 retracted sheath
540 guidewire
600 type-2 catheter
641 guidewire lumen
650 type-2 catheter body
660 balloon
660' inflated balloon
810 tailpiece
820 tailpiece distal end
861 slits or notches
870 injection tube
900 type-1 catheter
910 tailpiece
920 tailpiece distal end
961 injection array
962 needle projections
970 injection tube The following description and accompanying figures describe and show certain variations to demonstrate, in a nonlimiting manner, several possible configurations.

This document describes several incising catheters and systems for using dual-access catheters. For purposes of this disclosure, "dual-access" means devices or methods designed to access a vascular lesion from two separate vascular openings. In some cases, the separate vascular openings are above and below the lesion. As will be discussed below, one reason for using dual-access methods is to minimize the profile, diameter, or width of a percutaneous medical device. Smaller diameters lead to lower profiles relative to current cutting and scoring devices, which typically have a 4 French or larger diameter. Disclosed incising catheters provide controlled incision depths by controlling the pressure of an angioplasty balloon or by choosing appropriate blade or needle dimensions. Due to this improved control, these incising catheters safely cut, score, or incise tissue to a greater depth than current cutting and scoring devices. Typically, current devices cut or score vascular tissue to a depth of less than 0.5 mm.

In some variations, the incising component is activated or extended by a typical angioplasty balloon coming from a separate vascular opening, such as a vascular opening positioned above the target lesion. Coupling the balloon to the incising component can be accomplished by using a guidewire in some cases a single guidewire disposed through the incising or type-1 catheter and the balloon or type-2 catheter.

Synopsis of a Variation of the Device of the Method for Using the Device

In some variations, the type-1 catheter is a 3-6 French catheter that contains a blade that is 0.1-2 mm long. In these devices, the blade slices tissue (including arterial wall tissue) when activated by an angioplasty balloon. In some variations, the type-1 catheter is delivered to a lesion from either a vascular opening such that the catheter approaches the lesion from above or below the lesion. Type-2 catheters can be delivered from a vascular opening opposite that of the type-1 catheter. These two catheters are coupled together with a single guidewire before the incision process. In the incision process, the balloon is inflated and this increase in size drives the blade of the type-1 catheter into the lesion tissue. During the procedure, the tissue is sliced to a predetermined depth, controlled by blade height, but typically not exceeding arterial wall thickness. Use of these devices and procedures can occur in the vasculature of various body parts. The incising catheters have better effectiveness than current scoring and cutting balloons because current balloons have limited depth and have relatively blunt scoring components.

A variety of guidewires or guidewire sizes is useful for practicing these methods. Selecting guidewires or guidewire sizes is well within the capability of those of ordinary skill in the art when using these dual-access devices. For instance, these devices can use guidewires that have 0.014-0.018 inch diameters.

Described below is an exemplary procedure to treat BTK arteries, such as tibial arteries, using the subject devices.

An access sheath is inserted into an artery below the target lesion. The device inserted here will access the lesion from a downstream direction or from a direction opposite the blood-flow direction. An operator forms an access site above the lesion such as with femoral access on the same or the other leg and an access site below the lesion. Next, access sheaths are inserted. The type-2 catheter (4 French balloon) is introduced and threaded down towards the target lesion. A guidewire is introduced through the lower access site and advanced up and into the type-2 catheter distal tip. The guidewire is threaded through the catheter until it exits the type-2 catheter proximal end outside of the body leaving a single guidewire connecting the upper and lower access points. The type-1 catheter is then advanced to the lesion from below towards the type-2 catheter until they meet. Once they meet, the sheath can be retracted and the slicing procedure can be performed by inflating the balloon. Balloon inflation pushes the blade outwardly from inside the vessel to against the inner lumenal wall of the vessel. Before the balloon is inflated, the protrusion or blade edge or needle projections contact the lesion, but supply substantially no force to the lesion.

For purposes of this document, "substantially no force" means no force or some force depending on the particular catheter variation. In some variations, a relaxed configuration means the configuration of the type-1-type-2 catheter pair after delivery to the target lesion before balloon inflation. When "substantially no force" means some force, it includes outwardly directed force that is 0.1-50%, 0.1-40%, 0.1-30%, 0.1-20%, 0.1-10%, or 0.1-1% of an operative force. In some variations, substantially no force means an outward force that is 0.0-50%, 0.0-40%, 0.0-30%, 0.0-20%, 0.0-10%, or 0.0-1% of an operative force. In some variations, substantially no force means an outward force that is 0.0-50%, 0.0-40%, 0.0-30%, 0.0-20%, 0.0-10%, or 0.0-1% of typical angioplasty procedures. In some variations, "substantially no force" means any amount of force caused by the device being delivered to the lesion or being disposed next to the lesion before beginning balloon inflation. In some variations, "operative force" is the minimum amount of force necessary to fracture calcium deposits in the target lesion. In these or other variations, "operative force" is the minimum amount of force necessary to cut or slice lesion tissue. In some variations, an "activated configuration" means a configuration of the type-1-type-2 catheter pair after balloon to deliver "operative force".

Considered from the below-the-knee perspective, the tip of the guidewire is disposed near the distal end (bottom end) of the type-2 catheter, in some variations.

An operator advances a type-1 catheter up from the BTK or other downstream access until the end of the type-1 catheter is near the lesion. In some variations, the type-1 catheter upward end is near and below the target lesion.

The balloon is then advanced into or across the treatment location. Then the type-1 catheter is inserted until it reaches the vicinity of the balloon. The delivery sheath is retracted, the blade or protrusion of the type-1 catheter is rotated into a proper orientation relative to the lesion, and the balloon and the incising device are coupled. Thus, the type-1 catheter and the type-2 catheter are nested alongside the lesion.

At this point the balloon is inflated, driving the blade into the tissue. The operator can control the driving force with the balloon pressure. In situations where the treatment site is longer than the blade, the operator can reposition the device and repeat balloon inflation. Finally, the blade device is withdrawn from the artery.

In some variations, this procedure is followed by similar treatments, including a drug-coated balloon treatment where the drug-coated balloon is employed after the incision is made to deposit drugs such as paclitaxel on the incised lesion to prevent restenosis.

FIGS. 1A-3C illustrates a tailpiece 110 of a type-1 catheter. Along with tailpiece 110, a type-1 catheter comprises various tubing and handles (not shown) to facilitate delivery of tailpiece 110 to an intravascular lesion. A type-1 catheter also comprises a type-1 proximal end (not shown) at least part of which remains outside of the patient and at least part of which connects to tailpiece proximal end 115.

Tailpiece 110 has tailpiece proximal end 115, tailpiece distal end 120, and push region 122 located on a side of tailpiece 110. Push region 122 comprises balloon pocket 124, which is formed by removing a longitudinal portion of tailpiece 110 extending from tailpiece distal end 120 proximally, and ending short of tailpiece proximal end 115. Tailpiece distal end 120 also has protrusion or blade 130 positioned perpendicular to or at 90° to outer surface 123 of tailpiece distal end 120, or from 45-90°, from 60-90°, from 75-90°, or from 85-90° to outer surface 123. Protrusion or blade 130 is disposed on the side of tailpiece distal end 120 opposite push region 122. The removed portion can be defined by a chord of a circular portion of tailpiece 110 formed at 10-90%, 10-60%, 10-50%, or 10-40% of the diameter of tailpiece 110.

Balloon pocket 124 is adapted to receive balloon 660 from type-2 catheter 600, as will be discussed more fully below. "Adapted to receive" means that the structure has been modified to better receive or hold balloon 660 than similar structures that have not been adapted in this way. For instance, balloon pocket 124 may have a variety of adaptations including changes in length, width, depth, curvature, tackiness, sidewall height, etc. These adaptations facilitate holding balloon 660 in position as an operator inflates balloon 660 during use.

FIGS. 1A-3C also illustrates catheter distal tip 125 and blade edge 131. Balloon pocket 124 has a curved shape, complementary to the curved outer surface of an angioplasty balloon. This shape helps maintain registry between the balloon and the incising edge, blade, or needle projections.

FIG. 4 shows an alternative version of a type-1 catheter 400. This variation is similar to the variation described in FIGS. 1A-3C. FIG. 4 illustrates tailpiece 410 of type-1 catheter 400. Along with tailpiece 410, type-1 catheter 400 comprises various tubing and handles (not shown) to facilitate delivery of tailpiece 410 to an intravascular lesion.

Tailpiece 410 has tailpiece proximal end 415, tailpiece distal end 420, and push region 122 located on a side of tailpiece 410. Push region 122 comprises balloon pocket 124, which is formed by removing a longitudinal portion of tailpiece 410 extending from tailpiece distal end 420 proximally, and ending short of tailpiece proximal end 415. Tailpiece distal end 420 also has protrusion or blade 130 positioned perpendicular or at 90° to the outer surface 123 of tailpiece distal end 420, from 45-90°, from 60-90°, from 75-90°, or from 85-90° to outer surface 123. The removed portion can be defined by a chord of a circular portion of tailpiece 410 formed at 10-90%, 10-60%, 10-50%, or 10-40% of the diameter of tailpiece 410.

Balloon pocket 124 is adapted to receive balloon 660 from type-2 catheter 600. In addition to like-numbered elements depicting like-numbered components, this variation also depicts nose 430, catheter body 401, and flexible support 416. Flexible support 416 extends into catheter body 401.

Flexible support 416 has a relaxed position and an activated position. In the activated position, an inflated angioplasty balloon (not shown) from a separate catheter holds flexible support 416 outward or away from the longitudinal axis of type-1 catheter 400—the angioplasty balloon supplies the outwardly acting force. In some variations, nose 430 guides, directs, etc. balloon 660 into balloon pocket 124, guidewire 540 into guidewire lumen 641, or both of these.

FIG. 5 depicts a similar type-1 catheter 400 with tailpiece 410 as discussed above. FIG. 5 also depicts catheter body 501, sheath 530, and guidewire 540.

FIG. 6 depicts type-1 catheter 100, 400 paired with type-2 catheter 600. Type-2 catheter 600 has type-2 body 650 and balloon 660 located at its distal end. Type-2 catheter 600 has an opening in the distal end and has an appropriate opening to receive, direct, or guide guidewire 510, such as a funnel, guide piece, or generic opening, in some variations. Balloon pocket 124 engages or receives type-1, balloon 660 from type-2 catheter 600.

FIG. 7 depicts the type-1-type-2 catheter pair of FIG. 6 with inflated balloon 760. The figure illustrates tailpiece 410 of type-1 catheter 400. Along with tailpiece 410, type-1 catheter 400 comprises various tubing and handles (not shown) to facilitate delivery of tailpiece 410 to an intravascular lesion.

Tailpiece 410 has tailpiece proximal end 415, tailpiece distal end 420, and push region 122. Push region 122 is located on a side of tailpiece 410. Push region 122 comprises balloon pocket 124, which is formed by removing a longitudinal portion of tailpiece 410 extending from tailpiece distal end 420 proximally, and ending short of tailpiece proximal end 415. Tailpiece distal end 420 also has protrusion or blade 130 positioned perpendicular or at 90° to the outer surface 123 of tailpiece distal end 420, from 45-90°, from 60-90°, from 75-90°, or from 85-90° to outer surface 123. The removed portion can be defined by a chord of a circular portion of tailpiece 410 formed at 10-90%, 10-60%, 10-50%, or 10-40% of the diameter of tailpiece 410.

This figure illustrates the inflated balloon fitting into and being held or positioned by balloon pocket 124's shape.

FIG. 8 depicts a portion of an alternative variation of type-1 catheter 800 with inflated balloon 660 from type-2 catheter 600. Protrusion or blade 130 is disposed on the side of tailpiece distal end 120 opposite that of push region 122. The removed portion can be defined by a chord of a circular portion of tailpiece 110 formed at 10-90%, 10-60%, 10-50%, or 10-40% of the diameter of tailpiece 110.

Additionally, FIG. 8 shows that blade 130 and blade edge 131 comprise functionality to deliver fluid from blade edge 131 to the lesion. Fluid delivery notches or slits 861 are present along a portion of blade edge 131. Notches 861 connect with injection tube 870 providing a fluid delivery path from injection tube 870 to notches 861.

Figure 9:
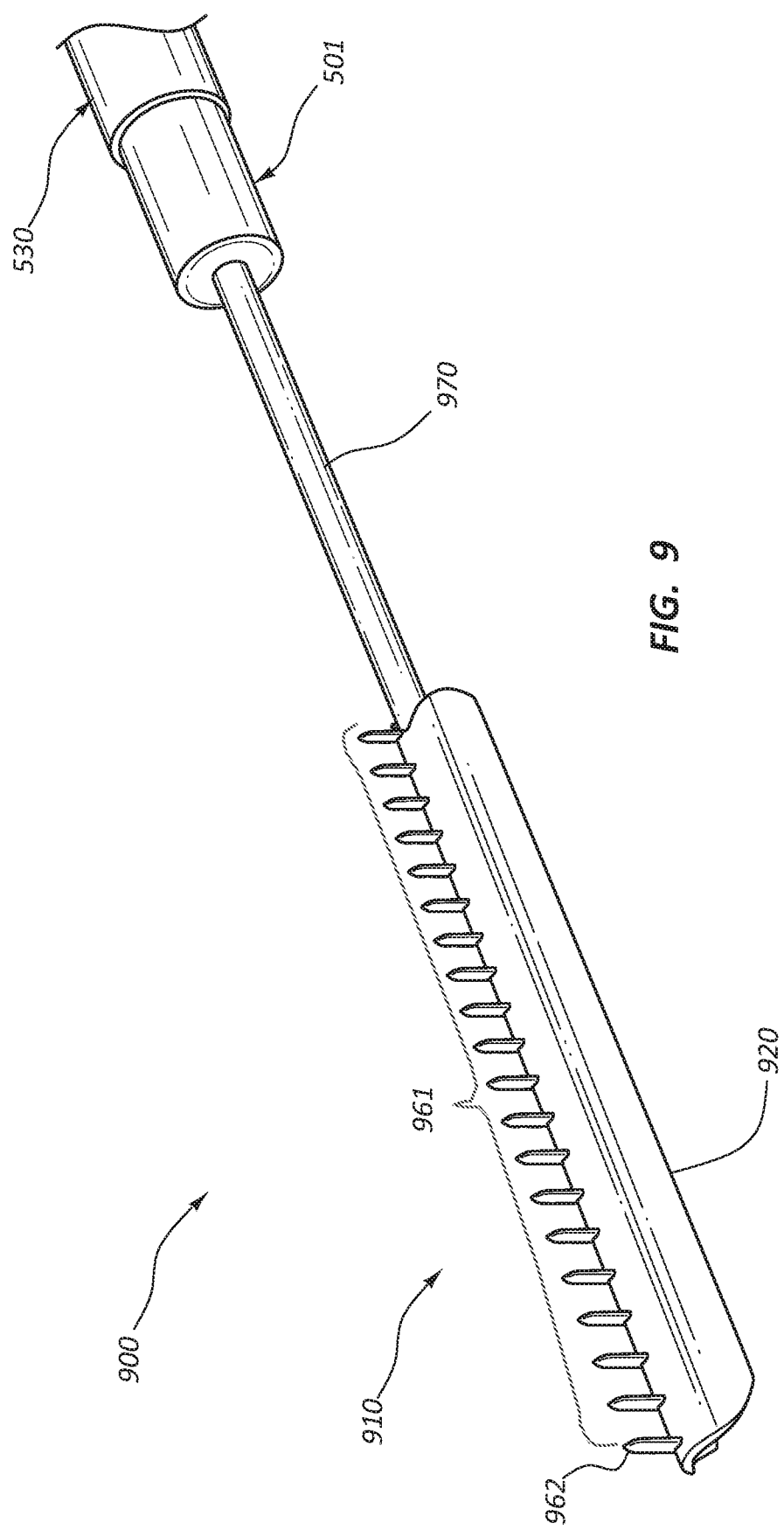
FIG. 9 is a perspective view of a type-1 catheter with an arrangement of needle projections.

FIG. 9 depicts an alternative version of the type-1 catheter 900. This figure shows tailpiece distal end 920 of type-1 catheter 900. This variation has a type-1 tailpiece 910 that is similar to type-1 tailpiece 110. It also comprises injection tube 970, which is similar to injection tube 870. Injection tube 970 delivers fluid to an array of injection array 961. Injection array 961 comprises one or more tubes or needle projections 962 in fluid communication with injection tube 970. These tubes or needle projections 962 use 34 gauge tubes, in some variations.

In some variations, type-1 catheter 100, 400 comprises a guide or funnel not shown to direct guidewire 540 into the distal end of the type-1 catheter guidewire lumen.

Type-1 catheters 100, 400 have elongated bodies and may contain any suitable biocompatible material. Also, type-1 catheters 100, 400 may contain typical materials including one or more of polymers such as polyethylene terephthalate (PET), polyetherimide (PEI), polyethylene (PE), polytetrafluoroethylene (PTFE), expanded polytetrafluoroethylene (ePTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), poly ether-ester, polyester, polyamide, elastomeric polyamides, block polyamide/ethers, polyether block amide, silicones, Marlex high-density polyethylene, Marlex low-density polyethylene, linear low density polyethylene, polyetheretherketones (PEEK), polyimide (PI), polyphenylene sulfide (PPS), polyphenylene oxide (PPO), polysulfone, nylon, or perfluoro(propyl vinyl ether) (PFA). Type-1 catheters 100, 400 also may be made from other suitable materials, or mixtures, combinations, copolymers, polymer-metal composites, and the like.

Type-2 catheters may be standard angioplasty balloon catheters or may be adapted for use with type-1 catheters or in systems with type-1 catheters. For example, in some variations, type-2 catheter 600 comprises a guide or funnel (not shown) to direct guidewire 540 into the distal end of the type-2 catheter guidewire lumen.

Type-2 catheters 600 have elongated bodies can contain any suitable biocompatible material. Also, type-2 catheters 600 can contain typical materials including one or more of polymers such as polyethylene terephthalate (PET), polyetherimide (PEI), polyethylene (PE), polytetrafluoroethylene (PTFE), expanded polytetrafluoroethylene (ePTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), poly ether-ester, polyester, polyamide, elastomeric polyamides, block polyamide/ethers, polyether block amide, silicones, Marlex high-density polyethylene, Marlex low-density polyethylene, linear low density polyethylene, polyetheretherketones (PEEK), polyimide (PI), polyphenylene sulfide (PPS), polyphenylene oxide (PPO), polysulfone, nylon, or perfluoro(propyl vinyl ether) (PFA). Type-2 catheters 600 also may contain other suitable materials, or mixtures, combinations, copolymers, polymer-metal composites, and the like.

Balloon 660 may contain any suitable biocompatible material. Also, balloon 660 may contain typical materials including one or more of polymers such as polyethylene terephthalate (PET), polyetherimide (PEI), polyethylene (PE), polytetrafluoroethylene (PTFE), expanded polytetrafluoroethylene (ePTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), poly ether-ester, polyester, polyamide, elastomeric polyamides, block polyamide/ethers, polyether block amide, silicones, Marlex high-density polyethylene, Marlex low-density polyethylene, linear low density polyethylene, polyetheretherketones (PEEK), polyimide (PI), polyphenylene sulfide (PPS), polyphenylene oxide (PPO), polysulfone, nylon, or perfluoro(propyl vinyl ether) (PFA). Balloon 660 also may contain other suitable materials, or mixtures, combinations, copolymers, polymer-metal composites, and the like.

Injection tubes 870, 970 comprise any suitable biocompatible polymer or metal.

Blade 130 comprises a sharp edge and support and is made from materials including Nitinol, stainless steel, titanium, cobalt-chromium, other metal alloys, and polymers.

Blade 130 may have a variety of lengths ranging from 1-200; 1-150; 1-100; 1-50; or 1-25 times the diameter of tailpiece 110. Blade 130 runs from tailpiece distal end 120 proximally or runs from a point proximal of tailpiece distal tip 125 a distance of 1-100, 5-80, 10-50, 5-40, 10-40, 5-20, 10-20 times the diameter of tailpiece 110. The length of blade 130 ranges from 1 to 500 mm or 20-40 mm. The height of blade 130 extending up from tailpiece distal end 120 ranges from 0.1 to 2 mm. The thickness of blade 130 need not be uniform along the blade and ranges from 0.025 to 0.25 mm.

Blade 130 has blade edge 131, which is sharpened along the region that is from 100%, 90%, 80%, 70%, or 50% of the length of blade 130. Blade edge 131 focuses force and yields potentially greater penetration as height increases. Blade 130 focuses force more as blade length decreases.

Nose 430 can be made of polymers such as polyether block amides (Pebax®; PEBAX is a registered trademark of AtoFina Chemicals), nylon, or polyurethane.

Tailpiece 110, 410 comprises material hard and stiff enough to form a rigid base for blade 130. In some variations, tailpiece 110, 410 is a metal, alloy, ceramic, or polymer material. Alternatively, tailpiece 110 is any one or any combination of the following materials: Nitinol, stainless steel, titanium, cobalt-chromium, other metal alloys, and polymers.

Blade 130 extends approximately perpendicular to tailpiece 110, 410. Depending on the catheter version, blade edge 131 exhibits a variety of sharpnesses ranging from dull to razor sharp. The sharpness of many versions are less than or much less than razor sharp. Also, variations in which blade edge 131 is not straight are within the scope of useful edges: wavy edges, toothed edges, triangularly toothed edges etc.

Notches 861 are from 0.1 to 5 mm wide along the length of blade 130 and are from 10% to 80% of the blade height high along the height of blade 130. In variations that use needle projections, 24 gauge tubes of from 0.1 to 3 mm long are useful, in many variations.

In operation, the operator opens an appropriate artery (or vein) below a target lesion. The operator inserts type-1 catheter into that access, access-1, and advances the catheter until tailpiece distal end 120 rests near the target lesion. The operator opens a second access, access-2, to an appropriate artery (or vein) above the target lesion. Then the operator inserts type-2 catheter 600 through the second access and advances the catheter until the distal end of catheter 600 is near the target lesion.

The operator tracks guidewire 540 through the type-1 catheter, passed the lesion until reaching the tip of the other catheter. The operator continues to advance guidewire 540 downward or upward until guidewire 540 exits the ex vivo end of the other catheter.

The operator captures the end of guidewire 540 into the other catheter. In some variations, the operator uses a funnel or capture device on the distal end of the catheter or nose 430 to facilitate guidewire capture.

The operator advances type-1 catheter 100 until blade 130 rests adjacent to the target lesion. And the operator advances type-2 catheter 600 until balloon 660 rests adjacent type-1 catheter, substantially entering balloon pocket 124 opposite of blade 130.

Once the operator is satisfied with the fit between balloon 660 and balloon pocket 124, the operator inflates balloon 660, forcing blade 130 into the lesion. The force of the inflating balloon substantially focuses on blade 130 and blade edge 131. The operator continues inflating the balloon, which causes blade 130 to apply more pressure. This pressure cuts or fractures hard portions of the lesion, such as calcium deposits, that blade 130 presses against. Cutting or fracturing results in a portion of the circumferential blood vessel receiving enough pressure to fracture, but the remainder of the circumference of the vessel remains protected from those higher pressures. In some variations, the operator repositions the type-1-type-2 catheter pair to move blade 130 to an adjacent, untreated portion of the lesion and then the operator repeats the inflation process. Alternatively, the operator may select the next untreated portion at a positions spaced apart from a previous treatment site.

In some variations, the operator opens the vessel below the lesion and advances type-1 catheter 400 until catheter distal tip 425 is near the target lesion. Once there, the operator inserts and advances guidewire 540 through type-1 catheter 400, past the lesion through to and out of a second access opening located up from the lesion. With guidewire access from access-1 below the lesion to access-2 above the lesion, the operator threads type-2 catheter onto guidewire 540 at access-2.

Next, the operator advances type-2 catheter over guidewire 540 until balloon 660 is near the target lesion. The operator adjusts the catheters until protrusion or blade 130 is inside of and inward of the target lesion, and moves the catheters together (end-to-end) until balloon 660 appropriately engages balloon pocket 124 in preparation of balloon inflation and the extension of protrusion or blade 130 into the lesion. Then, the operator inflates balloon 160, which forces protrusion or blade 130 against the lesion to focus the force of balloon inflation along blade or protrusion 130 against the lesion. The pressure of protrusion or blade 130 fractures the lesion, calcium deposits in the lesion, or both. The operator maintains this pressure as long as the operator deems to be appropriate for adequate treatment or efface-ment. In some variations, the operator maintains pressure for up to 5, 4, 3, 2, 1, 0.75, 0.5, or 0.25 minutes.

In other variations, the operator creates access-1 below the lesion and access-2 above the lesion. The operator inserts type-2 catheter into access-2 and tracks type-2 catheter down through the vasculature until balloon 660 reaches the lesion. The operator threads guidewire 540 down through a guidewire lumen of the type-2 catheter, past the lesion and the out of the dilator located at the other access site, in this instance, access-1. Afterwards, the operator tracks type-1 catheter over guidewire 540 until catheter distal tip 425 is near balloon 660 with both catheters on guidewire 540 and facing each other.

The operator then docks balloon 660 to or into type-1 catheter 100, 400, such as into balloon pocket 124, and adjusts protrusion or blade 130 to the treatment position. The operator inflates balloon 660, which pushes against the luminal wall of the vasculature near or at the lesion, but focused on protrusion or blade 130. After a treatment time, the operator deflates balloon 660.

When necessary, such as when treating longer lesions, the operator repositions the type-1-type-2 catheter pair to the next treatment site, sometimes an untreated site or an adjacent site. When choosing a second or subsequent treatment site, the operator can overlap protrusion or blade 130 with an already treated site or space the subsequent site some distance away from a previous treatment site, as desired. These process variations fracture or efface the target lesion or calcium deposits in the target lesion.

In other variations, guidewire 540, type-1 catheter 800, and type-2 catheter 600 are placed in ordinary target lesion, docked as described in any of the variations discussed above. But this family a variations has blade 130 with notches or slits 861 in blade edge 131. Once positioned, the operator inflates balloon 660 as described above or inflates balloon 660 in a way different from the variations described above, as the operator sees fit.

After placement, the operator administers a fluid through injection tube 870 causing it to flow out of slits 861 ultimately into the lesion. Administration time can run from 0.5-20, 1-10 10, 2-5, or 3-4 minutes or for as long as the operator sees fit.

In some variations, the fluid contains a therapeutic agent or combination of therapeutic agents, as listed below.

This family of processes fractures or effaces the lesion (or calcium deposits in the lesion) and afterwards delivers one or more therapeutic agents to the fracture or effacement site.

In another process variation, guidewire 540, type-1 catheter 800, and type-2 catheter 600 are placed near the treatment site and docked as described in any of the variations discussed above. But in this family of variations, protrusion 130 is an array of tubes extending vertically from tailpiece distal end 820, as shown in FIG. 9. These tubes or needle projections 962 have a variety of sharpnesses depending on the particular variation. When inflated, needle projections 962 focus inflation forces similar to the way that blade 130 or blade edge 131 focuses force, as discussed above. The inflation force focuses onto needle projections 962.

As with the variations discussed above using the injection array 961, the operator can discretionally reposition injection array 961 for subsequent treatments.

In some of these variations, after balloon 660 inflation, the operator injects fluid through injection tube 970 through injection array 961 and ultimately to the vascular tissue. Again, this yields a treatment process in which the operator first effaces or fractures the lesion (or calcium deposits in the lesion) and then supplies fluid to the effacement or fracture. As described above, the fluid can contain one or more therapeutic agents, depending on the variation. And treatment time can, as discussed above, depend on the variation.

Multiple variations in the process and devices have been discussed above. Some features can be combined with other variations in some cannot, as those of ordinary skill in the art will recognize. Variations and process steps have been described, as well. Many of age scratch that many variations are ambivalent to specific steps sequences. Those of ordinary skill in the art recognize which steps must be taken in order and which steps need not be taken in order. In some variations, all that matters is that the type-1 and type-2 catheter is assembled at the target lesion with the blade pointing in the correct direction to contact the lesion when the balloon inflates.

Bioactive agents can be added to the incising device (e.g., either by a coating or via a carrier medium such as resorbable polymers) for delivery to the host vessel or duct. The bioactive agents can be used to coat the device. A coating can include one or more nongenetic therapeutic agents; genetic materials and cells; and there combinations as well as other polymeric coatings. Nongenetic therapeutic agents include antithrombogenic agents such as heparins, heparin derivatives, urokinases, and PPack (dextrophenylalanine-proline-arginine chloromethylketone); antiproliferative agents such as enoxaprins, angiopeptins, or monoclonal antibodies capable of blocking smooth muscle cell proliferations, hirudins, and acetylsalicylic acids; antiinflammatory agents such as dexamethasones, prednisolones, corticosterones, budesonides, estrogens, sulfasalazines, and mesalamines; antineoplastic/antiproliferative/antimiotic agents such as paclitaxels, 5-fluorouracils, cisplatins, vinblastines, vincristines, epothilones, endostatins, angiostatins, and thymidine kinase inhibitors; anesthetic agents such as lidocaines, bupivacaines, and ropivacaines; anticoagulants; RGD peptide-containing compounds; antithrombin compounds; platelet receptor antagonists; antithrombin antibodies; antiplatelet receptor antibodies; aspirins; prostaglandin inhibitors; platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules with a growth factor and a cytotoxins, bifunctional molecules with an antibody and a cytotoxin; cholesterol-lowering agents; vasodilating agents; and agents which interfere with endogenous vascoactive mechanisms. Genetic materials include antisense DNA and RNA, DNA coding for antisense RNA, tRNA or rRNA to replace defective or deficient endogenous molecules, angiogenic factors including growth factors such as acidic and basic fibroblast growth factors; vascular endothelial growth factors; epidermal growth factors; transforming growth factor alpha and beta; platelet-derived endothelial growth factors; platelet-derived growth factors; tumor necrosis factor alphas; hepatocyte growth factor and insulin like growth factors; cell cycle inhibitors including CD inhibitors; thymidine kinase ("TK"); and other agents useful for interfering with cell proliferation; the family of bone morphogenic proteins ("BMPs"), BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or their combinations, alone or together with other molecules. Alternatively or in addition, molecules capable of inducing an upstream or downstream effect of a BMP can be provided. Such molecules include any of the "hedgehog" proteins, or the DNAs encoding them. Cells can be of human origin (autologous or allogeneic), or from an animal source (xenogeneic), genetically engineered if desired to deliver proteins of interest at the deployment site. The cells can be provided in a delivery media. The delivery media can be formulated as needed to maintain cell function and viability. Suitable polymer coating materials include polycarboxylic acids, cellulosic polymers, including cellulose acetate and cellulose nitrates, gelatins, polyvinylpyrrolidones, cross-linked polyvinylpyrrolidones, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalates, polyacrylamides, polyethers, polyether sulfones, polycarbonates, polyalkylenes including polypropylenes, polyethylenes and high molecular weight polyethylenes, halogenated polyalkylenes including polytetrafluoroethylenes, polyurethanes, polyorthoesters, proteins, polypeptides, silicones, siloxane polymers, polylactic acids, polyglycolic acids, polycaprolactones, polyhydroxybutyrate valerate and their blends and copolymers, coatings from polymer dispersions such as polyurethane dispersions (for example, BAYHDROL® fibrins, collagens, and their derivatives, polysaccharides such as celluloses, starches, dextrans, alginates and derivatives, hyaluronic acids, and squalene emulsions.

The invention claimed is:

1. An apparatus for incising a lesion in a vessel using an expandable device on a guidewire, comprising:
   a catheter including a body having a first portion with a guidewire lumen configured to receive the expandable device, and a second portion with a protrusion, the second portion of the body including an arc-shaped pocket defining only a single arc of a circumference of a circle, wherein a remainder of the circumference of the circle remains open, wherein the pocket is adapted for partially circumferentially surrounding the expandable device only on a single portion of a circumference of the expandable device such that a remainder of the circumference of the expandable device is not contacted by the catheter, and the protrusion extends from the second portion of the body and is adapted for incising the lesion upon expansion of the expandable device;

wherein the arc-shaped pocket defines a lateral opening along the second portion, said lateral opening being continuous with a distal-facing opening on a distal end of the second portion.

2. The apparatus of claim 1, wherein the protrusion of the body includes a focused force element adapted to incise the lesion, the focused force element including a push region adapted to engage the expandable device and push the focused force element toward the lesion upon expansion of the expandable device.

3. The apparatus of claim 2, wherein the focused force element comprises an edge for incising the lesion and a pocket opposite the edge adapted for receiving the expandable device.

4. The apparatus of claim 2, wherein the body of the catheter comprises a flexible support supporting the focused force element, the flexible support having a relaxed position and an activated position whereby the focused force element is advanced toward the lesion.

5. The apparatus of claim 4, further including a nose connected to a distal end of the flexible support, the nose forming a receiver adapted for receiving the guidewire.

6. The apparatus of claim 5, wherein a proximal end of the flexible support extends into the catheter and a distal end of the flexible support is connected to a proximal end of the nose.

7. The apparatus of claim 2, wherein the focused force element includes openings, and further comprising an injection tube in fluid communication with the openings.

8. The apparatus of claim 1, wherein the catheter does not include a balloon.

9. An apparatus for incising a lesion in a vessel using an expandable device on a guidewire, comprising:
a catheter including the following structures positioned in order from a proximal portion to a distal portion thereof:
(i) a body including a guidewire lumen;
(ii) a focused force element connected to the body, the focused forced element including an arc-shaped pocket defining only a single arc of a circumference of a circle, wherein a remainder of the circumference of the circle remains open, wherein the pocket is adapted for partially circumferentially surrounding the expandable device only on a single portion of a circumference of the expandable device such that a remainder of the circumference of the expandable device is not contacted by the catheter; and
(iii) a nose connected to the focused force element, the nose defining a channel therethrough, wherein the channel includes a lateral opening extending along a longitudinal length of the channel on a radially outer portion of the channel; and
a flexible support supporting the focused force element, the nose is connected to a distal end of the flexible support to be spaced apart from the focused force element;
wherein the nose extends outward in a radial direction farther than the flexible support.

10. The apparatus of claim 9, wherein the flexible support comprises a first portion connected to the body proximal of the focused force element and a second portion connected to the nose including the channel.

11. The apparatus of claim 9, wherein the focused force element comprises a blade having an edge and a curved push region opposite the edge adapted to partially surround the expandable device.

* * * * *